US011202795B2

(12) United States Patent
Verstreken et al.

(10) Patent No.: US 11,202,795 B2
(45) Date of Patent: Dec. 21, 2021

(54) MEANS AND METHODS FOR TREATMENT OF EARLY-ONSET PARKINSON'S DISEASE

(71) Applicants: VIB VZW, Ghent (BE); Katholieke Universiteit Leuven, K.U.Leuven R&D, Leuven (BE)

(72) Inventors: Patrik Verstreken, Blanden (BE); Vanessa Morais Epifânio, Kessel-Lo (BE); Melissa Vos, Noorderwijk (BE)

(73) Assignees: VIB VZW, Ghent (BE); Katholieke Universiteit Leuven, KU Leuven R&E, Leuven (BE)

( * ) Notice: Subject to any disclaimer, the term of this patent is extended or adjusted under 35 U.S.C. 154(b) by 0 days.

(21) Appl. No.: 15/525,566

(22) PCT Filed: Nov. 20, 2015

(86) PCT No.: PCT/EP2015/077263
§ 371 (c)(1),
(2) Date: May 9, 2017

(87) PCT Pub. No.: WO2016/079317
PCT Pub. Date: May 26, 2016

(65) Prior Publication Data
US 2017/0319610 A1 Nov. 9, 2017

(30) Foreign Application Priority Data

Nov. 20, 2014 (EP) .................................... 14194027

(51) Int. Cl.
A61K 31/713 (2006.01)
A61K 31/7105 (2006.01)
C12N 9/10 (2006.01)

(52) U.S. Cl.
CPC ........ *A61K 31/713* (2013.01); *A61K 31/7105* (2013.01); *C12N 9/1029* (2013.01); *C12Y 203/01085* (2013.01)

(58) Field of Classification Search
CPC .......................... A61K 31/713; A61K 31/7105
See application file for complete search history.

(56) References Cited

U.S. PATENT DOCUMENTS

| 5,011,472 | A | 4/1991 | Aebischer et al. | |
| 5,023,252 | A | 6/1991 | Hseih | |
| 2003/0143732 | A1 | 7/2003 | Fosnaugh et al. | |
| 2007/0027208 | A1* | 2/2007 | Caron | A61K 31/137 514/464 |
| 2007/0066527 | A1* | 3/2007 | Tezapsidis | A61K 38/17 514/5.8 |
| 2013/0267558 | A1 | 10/2013 | Kim et al. | |

FOREIGN PATENT DOCUMENTS

| EP | 2716652 A1 | 4/2014 |
| WO | 2004005277 A1 | 1/2004 |
| WO | 2004034991 A2 | 4/2004 |
| WO | 2005117590 A2 | 12/2005 |
| WO | 2007014247 A2 | 2/2007 |
| WO | 2007014249 A2 | 2/2007 |
| WO | 2008057585 A1 | 5/2008 |
| WO | 2009149066 A1 | 12/2009 |
| WO | 2011005790 A1 | 1/2011 |
| WO | 2011048018 A1 | 4/2011 |
| WO | 2012064632 A1 | 5/2012 |
| WO | 2013022927 A2 | 2/2013 |
| WO | 2013155528 A1 | 10/2013 |
| WO | 2014039769 A1 | 3/2014 |
| WO | 2014164749 A1 | 10/2014 |
| WO | 2014164767 A1 | 10/2014 |
| WO | 2015084606 A1 | 6/2015 |
| WO | 2015095011 A1 | 6/2015 |
| WO | 2015134790 A1 | 9/2015 |
| WO | 2016079317 | 5/2016 |

OTHER PUBLICATIONS

Lee et. al. (Trends in Pharmacological Sciences (2012) 33:365-373). (Year: 2012).*
Valente et. al. (Science (2004) 304:1158-1160). (Year: 2004).*
Whitworth et al., Drosophila models pioneer a new approach to drug discovery for Parkinson's disease, Drug Discovery Today, Feb. 2006, pp. 119-126, vol. 11, No. 3/4, Elsevier.
Byoung Dae Lee et al., Leucine-rich repeat kinase 2 (LRRK2) as a a potential therapeutic target in Parkinson's disease, Trends in Pharmaacological Sciences, Jul. 2012, pp. 365-373, vol. 33, No. 7, Elsevier Ltd.
PCT International Search Report dated Feb. 11, 2016, dated Feb. 19, 2016, PCT/EP2015/077263.
PCT Written Opinion of the International Searching Aurthority dated Feb. 11, 2016, dated Feb. 19, 2016, PCT/EP2015/077263.
F. Blandini et al., Animal model of Parkinson's disease, The FEBS Journal, 2012, pp. 1156-1166, vol. 279, The Authors Journal compilation.
European Patent Office Communication Pursuant to Article 94(3) EPC, Application No. 15797678.8, dated Nov. 21, 2018, 8 pages.
Ferretta et al., "Effect of resveratrol on mitochondrial function: Implications in parkin-associated familiar Parkinson's disease", Biochimica Et Biophysica Acta. Molecular Basis of Disease, vol. 1842, No. 7, Feb. 25, 2014 (Feb. 25, 2014), pp. 902-915, XP028650661, ISSN: 0925-4439, DOI: 10.1016/J.BBADIS.2014.02.010.
Liang et al. "Inhibitory effects of grape skin extract and resveratrol on fatty acid synthase", BMC Complementary and Alternative Medicine, Biomed Central Ltd., London, GB, vol. 13, No. 1, Dec. 16, 2013 (Dec. 16, 2013), p. 361, XP021171190, ISSN: 1472-6882, DOI: 10.1186/1472-6882-13-361.

(Continued)

*Primary Examiner* — Marcos L Sznaidman
(74) *Attorney, Agent, or Firm* — Patent Law Works, LLP

(57) ABSTRACT

This application relates to the field of neurodegenerative diseases, more particularly to the field of Parkinson's disease. In particular, the disclosure describes that inhibitors reducing FAS activity can be used for treatment of Parkinson's disease, in particular, the treatment of patients suffering from Parkinson's disease having loss of function mutations in PINK1 or PARKIN genes.

6 Claims, 5 Drawing Sheets

(56) References Cited

OTHER PUBLICATIONS

Ng et al., "AMP Kinase Activation Mitigates Dopaminergic Dysfunction and Mitochondrial Abnormalities in *Drosophila* Models of Parkinson's Disease", The Journal of Neuroscience, vol. 32, No. 41, Oct. 10, 2012 (Oct. 10, 2012), pp. 14311-14317, XP055523161, US ISSN: 0270-6474, DOI: 10.1523/JNEUROSCI.0499-12.2012.

Reddy et al. "Neuroprotective Effect of Green Tea Polyphenol, EGCG in Animal Model of Parkinson's Disease", The FASEB Journal, Federation of American Societies for Experimental Biology, US, vol. 22, No. 2, supplement, Apr. 1, 2008 (Apr. 1, 2008 ), XP009509320, ISSN: 0892-6638.

Yupin et al. "Anti-oxidant polydatin (piceid) protects against substantia nigral motor degeneration in multiple rodent models of Parkinson?s disease", Molecular Neurodegeneration, Biomed Central Ltd, LO, vol. 10, No. 1, Mar. 2, 2015 (Mar. 2, 2015), p. 4, XP021217832, ISSN: 1750-1326, DOI: 10.1186/1750-1326-10-4.

Zhang, et al. "Polydatin alleviates non-alcoholic fatty liver disease in rats by inhibiting the expression of TNF-[alpha] and SREBP-1 c", Molecular Medicine Reports, vol. 6, No. 4, Jul. 31, 2012 (Jul. 31, 2012 ), pp. 815-820, XP055523150, GR ISSN: 1791-2997, DOI: 10.3892/mmr.2012.1015.

Ng et al. "EGCG and CGA mitigate neurological phenotypes in Drosophila models of Parkinson's disease", Abstracts of the Annual Meeting of the Society for Neuroscience, Society for Neuroscience, US, vol. 40, No. Program#/Poster#: 858.7/J20, Jan. 1, 2010, 2 pgs. https://bit.ly/3wEfi0W \* cited by examiner

MEANS AND METHODS FOR TREATMENT OF EARLY-ONSET PARKINSON'S DISEASE

CROSS-REFERENCE TO RELATED APPLICATIONS

This application is a national phase entry under 35 U.S.C. § 371 of International Patent Application PCT/EP2015/077263, filed Nov. 20, 2015, designating the United States of America and published in English as International Patent Publication WO 2016/079317 A1 on May 26, 2016, which claims the benefit under Article 8 of the Patent Cooperation Treaty to European Patent Application Serial No. 14194027.0, filed Nov. 20, 2014.

TECHNICAL FIELD

This application relates to the field of medicine and neurodegenerative diseases, more particularly, to the field of Parkinson's disease. In particular, it has been found that inhibitors reducing FAS activity can be used for treatment of Parkinson's disease, in particular, the treatment of patients suffering from early-onset Parkinson's disease, more particularly, Parkinson's disease patients having loss of function mutations in the PINK1 or PARKIN gene.

BACKGROUND

Parkinson's disease (PD) is a progressive neurodegenerative disease characterized by tremor, rigidity, bradykinesia, and postural instability. Most forms of Parkinson's disease are sporadic; however, ~5% cases are attributed to mutations in several genes leading to early onset or familial forms of the disease. Mutations in α-SYNUCLEIN, PARKIN, UCH-L1 (ubiquitin-C terminal hydrolase-L1), DJ-1, PINK1 (PTEN-induced kinase 1), and LRRK2 (leucine-rich repeat kinase 2) have been found in familial forms and/or early-onset PD. Both genetic and environmental factors are likely to contribute to risk of PD. PINK1 is a mitochondrial kinase thought to be involved in mitochondrial quality control. The identification of this gene as well as several other ones (such as PARKIN) led to the idea that mitochondrial dysfunction may be a central culprit to the disease. In *Drosophila melanogaster*, loss of PINK1 function results in very clear phenotypes, including reduced flight ability and mitochondrial defects such as reduced Complex I activity of the electron transport chain that results in reduced ATP levels and disruption of the mitochondrial membrane potential as well as defective mitochondrial morphology. An estimated 1% to 7% frequency of PINK1 mutations has been demonstrated among early-onset PD (EOPD) or autosomal recessive PD (ARPD) in Caucasians (Tan Eng-King et al. (2006) Movement Disorders 21, 6, 789). Aside from its function in Complex I, PINK1 is also identified as a factor in the clearance of defective mitochondria (=mitophagy) together with PARKIN, another protein involved in PD. PARKIN is a 465 amino acid protein. The gene encoding for PARKIN is widely expressed throughout the brain and functions as a ubiquitin ligase that attaches ubiquitin molecules to misfolded proteins in order to flag them for proteasomal processing. This system is thought to be important in protein degradation and later deposition of alpha-synuclein into brain tissue. Mutations within the PARKIN gene are also known to cause early-onset Parkinson's disease (EOPD), particularly in patients who develop symptoms prior to the age of 40. One of the most striking differences between homozygous mutation carriers of PARKIN or PINK1 and heterozygous mutation carriers for these genes is the earlier stage of onset (approximately 20 years prior to the heterozygote onset) for the homozygous disease carriers. The current treatment options for PINK1 and PARKIN mutation carriers are limited and there is a need to identify novel compounds that can modify the disease.

SUMMARY OF THE DISCLOSURE

This disclosure satisfies this need and shows that the use of Fatty acid synthase (FAS) inhibitors can be used as a medicament for the treatment of early-onset Parkinson's disease patients, more particularly, Parkinson's disease patients carrying PINK1 and PARKIN mutations.

DETAILED DESCRIPTION

Figure 1:
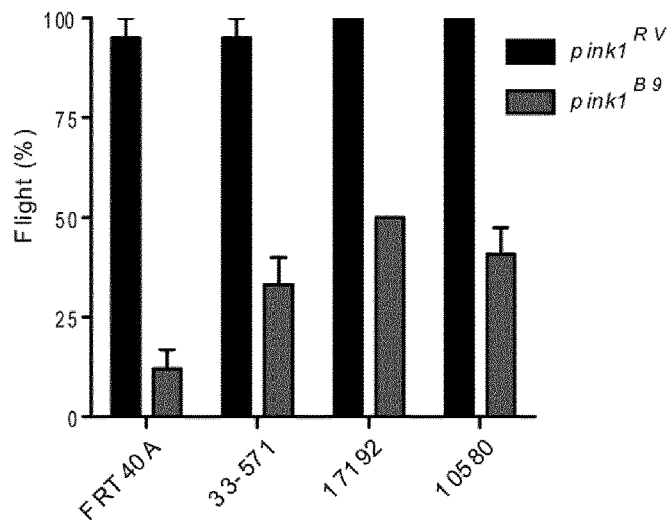
FIG. 1: Flight ability of controls (PINK1$^{RV}$) and hemizygous PINK$^{B9}$ mutant males heterozygous for v(2)k05816. FRT40A is a control allele; 33-571 is an EMS-induced allele that was identified in the modifier screen; 17192 and 10580 are P element insertions. Heterozygous mutations for v(2) k05816 do not induce a flight defect (black bars) and combined with PINK1 mutants, it induces a rescue (gray bars).

As used herein, each of the following terms has the meaning associated with it in this section. The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or ±10%, more preferably 5%, even more preferably ±1%, and still more preferably ±0.1% from the specified value, as such variations are appropriate to perform the disclosed methods. The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type. The drawings described are only schematic and are non-limiting. In the drawings, the size of some of the elements may be exaggerated and not drawn to scale for illustrative purposes. Where the term "comprising" is used in the present description and claims, it does not exclude other elements or steps. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Unless specifically defined herein, all terms used herein have the same meaning as they would to one skilled in the art of this disclosure. Practitioners are particularly directed to Sambrook et al., *Molecular Cloning: A Laboratory Manual*, 4$^{th}$ ed., Cold Spring Harbor Press, Plainsview, N.Y. (2012); and Ausubel et al., *Current Protocols in Molecular Biology* (Supplement 100), John Wiley & Sons, New York (2012), for definitions and terms of the art. The definitions provided herein should not be construed to have a scope less than understood by a person of ordinary skill in the art.

This disclosure surprisingly shows that the inhibition of fatty acid synthase (FAS) can be used to reduce Complex I defects in cells derived from Parkinson's disease patients, which cells have a loss of function mutation in the genes PINK1 and/or PARKIN. In a particular aspect, this loss of function is present in a heterozygous state. In another particular aspect, this loss of function is present in a homozygous state.

Assays to measure the loss of function of PINK1 or PARKIN are described in the art and are known by the skilled person. For example, a PINK1 assay is described by A. Beilina and M. R. Cookson, *Protein Kinase Technologies, Neuromethods* Vol. 68, 2012, pp. 219-236. For example, a PARKIN assay is described by A. Agne Kazlauskaite et al (2014) Open Biol. 4, p. 130213. Alternatively, a homozygous or heterozygous carrier for PINK1 or PARKIN loss of function mutation can be identified by sequencing the genes encoding for PINK1 or PARKIN.

Figure 8:
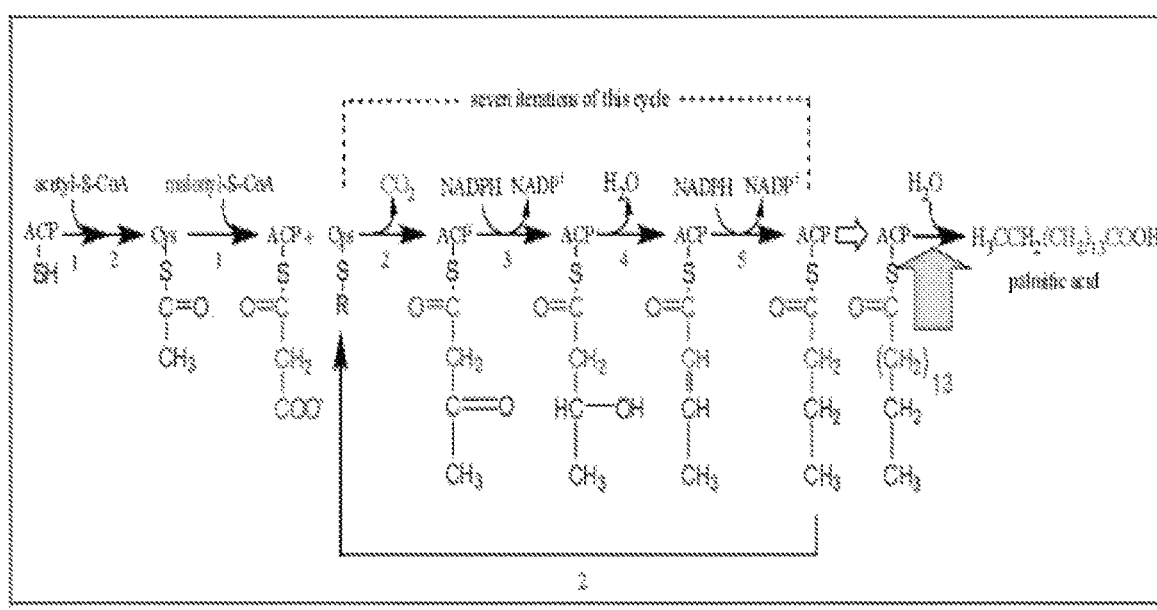
FIG. 8: Scheme of the enzymatic steps conducted by FAS involved in palmitate biosynthesis.

Fatty acid synthase (FAS) is the single human enzyme that can convert dietary carbohydrate to fat. FAS consists of six enzymatic domains and an acyl-carrier protein (ACP) that work together to perform the following chemical steps leading to synthesis of palmitate (see FIG. 8). The malonyl/acetyl transferase domain (1) transfers an acetyl group onto the ACP. It is then translocated to the active-site cysteine by α-ketoacyl synthase (2). This position, marked "R," also serves as the loading position for the growing acyl chain in subsequent iterations. The malonyl/acetyl transferase domain (1) then transfers a malonyl group to the ACP, and the two are condensed (2) into a four-carbon product bound to the enzyme through the thiol of the ACP. The ketoacyl reductase (3) reduces the ketone at C-3 to an alcohol. The dehydrase (4) further reduces the alcohol to an alkene. The enoyl reductase domain (5) further reduces the alkene bond to an alkane, and the ACP-bound chain is translocated back to the active-site cysteine (2). Steps 2-5 are then repeated six times to yield a 16-carbon, fully saturated palmitic acid bound to the ACP. The palmitate is released from FAS by the enzyme's intrinsic thioesterase domain (see arrow).

FAS is minimally expressed in most normal human tissues except the liver and adipose tissue, where it is expressed at high levels. Increased expression of FAS is a hallmark of all major cancers (prostate, breast, colon and ovarian) and is usually linked with poor prognosis. In addition, FAS expression is also closely linked to obesity, and has a high expression in adipose tissue. FAS expression in human liver is even higher and the capacity of synthesizing fatty acid in liver is 8 to 9 times higher than that in adipose tissue. It is shown in the art that specific small molecule inhibitors of FAS can reduce the synthesis of fatty acids by inhibiting the FAS. In addition, FAS inhibitors can also improve non-insulin-dependent diabetes, reduce high blood pressure, coronary thrombosis and other symptoms of complications of obesity, reducing incidences thereof. Currently, a number of chemical substances are known to inhibit FAS.

Accordingly, in a first embodiment, the disclosure provides a compound inhibiting FAS for the treatment of Parkinson's disease patients having a loss of function in the PINK1 gene. In yet another embodiment, the disclosure provides a compound inhibiting FAS for the treatment of Parkinson's disease patients having a loss of function in the PARKIN gene. In yet another embodiment, the disclosure provides a compound inhibiting FAS for the treatment of Parkinson's disease having a loss of function in the PINK1 gene or in the PARKIN gene.

In a particular embodiment, loss of function in the PINK1 or in the PARKIN gene is present in a heterozygous state. In yet another particular embodiment, loss of function in the PINK1 or in the PARKIN gene is present in a homozygous state.

A compound inhibiting FAS (alternatively, a FAS inhibitor) can be a chemical compound, an siRNA with a specificity for FAS, a ribozyme inhibiting FAS, an antisense molecule inhibiting FAS, a peptide inhibiting FAS, a peptidomimetic inhibiting FAS, or an artificial microRNA targeting FAS for the treatment of Parkinson's disease having a loss of function in the PINK1 gene or in the PARKIN gene.

In yet another embodiment, the siRNA, or antisense molecule, or ribozyme with a specificity for FAS is expressed by an expression construct, which is further incorporated into a gene therapy vector. A gene therapy vector can be a viral or a non-viral vector. Examples of viral vectors include adenoviral, adeno-associated vectors, lentiviral vectors and the like.

In a specific embodiment, the siRNA with a specificity for FAS is expressed by an expression construct incorporated into an adenoviral-2 associated (AAV-2) vector.

The term "siRNA" refers to a small interfering RNA(s), which also has been referred to in the art as short interfering RNA and silencing RNA, among others. siRNAs generally are described as relatively short, often 20-25 nucleotide-long, double-stranded RNA molecules that are involved in RNA interference (RNAi) pathway(s). Generally, siRNAs are, in part, complementary to specific mRNAs (such as FAS) and mediate their down-regulation (hence, "interfering"). siRNAs thus can be used for down-regulating the expression of specific genes and gene function in cells and organisms. siRNAs also play a role in related pathways. The general structure of most naturally occurring siRNAs is well established. Generally, siRNAs are short double-stranded RNAs, usually 21 nucleotides long, with two-nucleotide single-stranded "overhangs" on the 3' of each strand. Each strand has a 5' phosphate group and a 3' hydroxyl (—OH) group. In vivo, the structure results from processing by the enzyme "dicer," which enzymatically converts relatively long dsRNAs and relatively small hairpin RNAs into siRNAs. The term "siNA" refers to a nucleic acid that acts like an siRNA, as described herein, but may be other than an RNA, such as a DNA, a hybrid RNA:DNA, or the like. siNAs function like siRNAs to down-regulate expression of gene products. The term "RNA interference," which also has been called "RNA mediated interference," refers to the cellular processes by which RNA (such as siRNAs) down-regulate expression of genes; i.e., down-regulate or extinguish the expression of gene functions, such as the synthesis of a protein encoded by a gene. Typically, double-stranded ribonucleic acid inhibits the expression of genes with complementary nucleotide sequences. RNA interference pathways are conserved in most eukaryotic organisms. It is initiated by the enzyme dicer, which cleaves RNA, particularly double-stranded RNA, into short double-stranded fragments 20-25 base pairs long. One strand of the double-stranded RNA (called the "guide strand") is part of a complex of proteins called the RNA-induced silencing complex (RISC). The thus incorporated guide strand serves as a recognition sequence for binding of the RISC to nucleic acids with complementary sequences. Binding by RISC to complementary nucleic acids results in their being "silenced." The best studied silencing is the binding of RISCs to RNAs resulting in post-transcriptional gene silencing. Regardless of mechanism, interfering nucleic acids and RNA interference result in down-regulation of the target gene or genes that are complementary (in pertinent part) to the guide strand. A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. The polynucleotide can be a sequence whose presence or expression in a cell alters the expression or function of cellular genes or RNA.

In addition, this disclosure contemplates polynucleotide-based expression inhibitors of FAS, which may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids.

SiRNA comprises a double-stranded structure typically containing 15 to 50 base pairs and preferably 19 to 25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise a sequence that is complimentary to a gene or mRNA. Antisense polynucleotides include, but are not limited to: morpholinos, 2'-O-methyl polynucleotides, DNA, RNA, and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited. Polynucleotides may contain an expression cassette coded to express a whole or partial protein, or RNA. An expression cassette refers to a natural or recombinantly produced polynucleotide that is capable of expressing a sequence. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences. The polynucleotide may contain sequences that do not serve a specific function in the target cell but are used in the generation of the polynucleotide. Such sequences include, but are not limited to, sequences required for replication or selection of the polynucleotide in a host organism.

Based on the RNA sequence of FAS, siRNA molecules with the ability to knock down FAS activity can be obtained by chemical synthesis or by hairpin siRNA expression vectors. There are numerous companies that provide the supply of custom-designed siRNAs on a given RNA sequence, e.g., AMBION®, IMGENEX™, and DHARMACON®.

The FAS siRNAs of the disclosure may be chemically modified, e.g., as described in US 2003/0143732, by phosphorothioate internucleotide linkages, 2'-O-methyl ribonucleotides, 2'-deoxy-2'fluoro ribonucleotides, "universal base" nucleotides, 5-C-methyl nucleotides, and inverted deoxyabasic residue incorporation. The sense strand of FAS siRNAs may also be conjugated to small molecules or peptides, such as membrane-permeant peptides or polyethylene glycol (PEG). Other siRNA conjugates that form part of this disclosure include cholesterol and alternative lipid-like molecules, such as fatty acids or bile-salt derivatives.

In a further embodiment, the disclosure relates to an expression vector comprising any of the above-described polynucleotide sequences encoding at least one FAS siRNA molecule in a manner that allows expression of the nucleic acid molecule, and cells containing such vector. The polynucleic acid sequence is operably linked to regulatory signals (promoters, enhancers, suppressors, etc.) enabling expression of the polynucleic acid sequence and is introduced into a cell preferably utilizing recombinant vector constructs. A variety of viral-based systems are available, including adenoviral, retroviral, adeno-associated viral, lentiviral, and herpes simplex viral vector systems. Selection of the appropriate viral vector system, regulatory regions and host cell is common knowledge within the level of ordinary skill in the art.

As gene delivery and gene silencing techniques improve, the selective deletion of FAS, in particular, in neuronal tissues, may prove useful in order to limit the impact of protein deletion to a particular system under study. The FAS siRNA molecules of the disclosure may be delivered by known gene delivery methods, e.g., as described in US 2003/0143732, including the use of naked siRNA, synthetic nanoparticles composed of cationic lipid formulations, liposome formulations including pH-sensitive liposomes and immunoliposomes, or bioconjugates including siRNAs conjugated to fusogenic peptides. Delivery of siRNA expressing vectors can also be systemic, such as by intravenous or intramuscular administration or by intrathecal or by intracerebral injection that allows for introduction into the desired target cell (see US 2003/0143732).

In yet another embodiment, the compound is a small molecule compound able to inhibit the enzyme FAS for the treatment of Parkinson's disease patients having a loss of function in the PINK1 gene or in the PARKIN gene.

In yet another specific embodiment, a compound is a peptide inhibiting the enzymatic activity of FAS. For example, EP2716652 (Tianjin Toptech Bioscience (CN)) describes peptides (16 amino acids) that are able to inhibit FAS transcription.

In a specific embodiment, a compound is a chemical molecule, particularly a small molecule, inhibiting the enzymatic activity of FAS for the treatment of Parkinson's disease patients having a loss of function in PINK1 and/or PARKIN. A non-limiting list of small molecules inhibiting FAS activity is shown below.

Cerulin is a natural antibiotic product of the fungus *Cephalosporium cerulean*. Cerulin inhibits the first enzymatic step of mammalian FAS. The structure of cerulin is shown below:

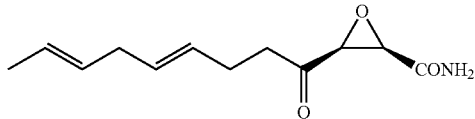 [SMILES: C/C=C/C/C=C/CCC(=O)[C@H]1O[C@H]1C(N)=O]

C-75, is a variant of cerulin, and inhibits FAS. The structure of C-75 is shown below:

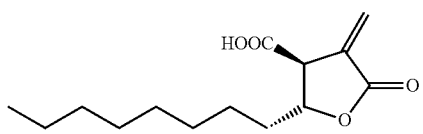

Yet another FAS inhibitor is orlistat, which is marketed as an anti-obesity drug. Orlistat inhibits FAS through the interaction with the TE domain. The structure of orlistat is shown below:

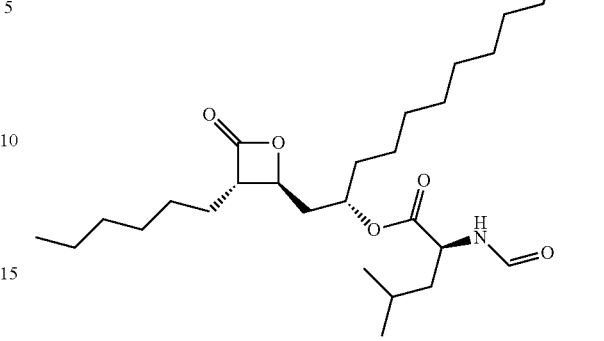

Yet another FAS inhibitor is EGCG (green tea polyphenol). The structure of EGCG is shown below:

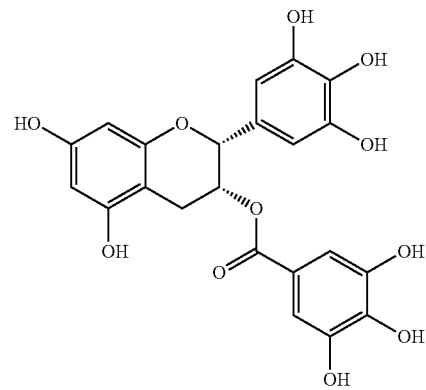 [SMILES: O=C(O[C@@H]1Cc2c(O)cc(O)cc2O[C@@H]1c1cc(O)c(O)c(O)c1)c1cc(O)c(O)c(O)c1]

Yet another FAS inhibitor is irgasan (or triclosan). Irgasan inhibits the enoyl-ACP (acyl-carrier protein) reductase component of FAS (step 4). Its structure is shown below:

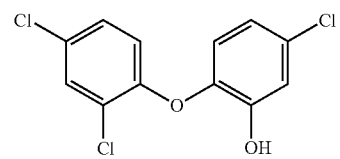 [SMILES: Oc1cc(Cl)ccc1Oc1ccc(Cl)cc1Cl]

Yet another FAS inhibitor is GSK837149A. This compound targets the beta-keto acyl reductase reaction)—step 2. Its structure is shown below:

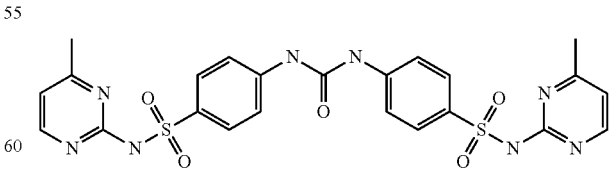

Yet another FAS inhibitor is cilostazol, which is also a phosphodiesterase inhibitor. Cilostazol is on the market (Otsuka Pharmaceuticals) for the treatment of intermittent claudication. Cilostazol is described to inhibit FAS (see US 2013/0267558). Its structure is shown below:

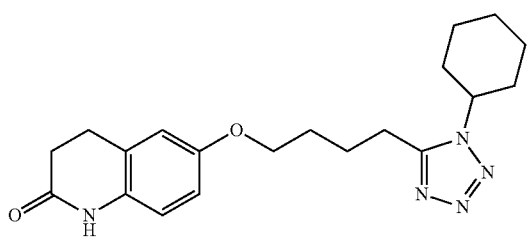 [SMILES: O=C1CCc2cc(OCCCCc3nnnn3C3CCCCC3)ccc2N1]

Yet another FAS inhibitor is orlipastat (Xenical, lipstatin), commercialized by Roche as an anti-obesity drug. Its structure is shown below:

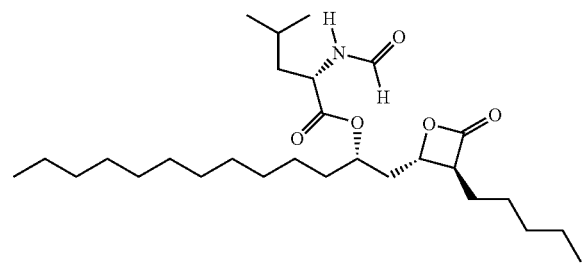 [SMILES: CCCCCCCCCCC[C@@H](C[C@@H]1OC(=O)[C@H]1CCCCC)OC(=O)[C@H](CC(C)C)NC=O]

Yet another example of a FAS inhibitor is PF-429242. The structure of which is shown below:

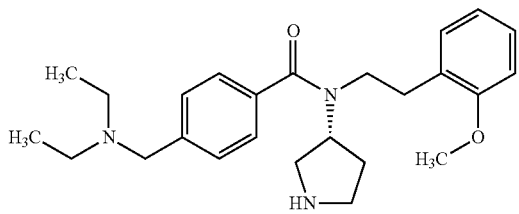 [SMILES: CCN(CC)Cc1ccc(C(=O)N(CCc2ccccc2OC)[C@@H]2CCNC2)cc1]

Yet another example of FAS inhibitors are polyphenolic compounds as derivatives of EGCG, which are described in C. Turrado et al. (2012) *J. of Med. Chem.* 55, 5013. An example of the structure of such a polyphenolic compound is shown below:

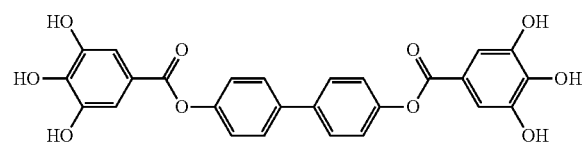 [SMILES: O=C(Oc1ccc(-c2ccc(OC(=O)c3cc(O)c(O)c(O)c3)cc2)cc1)c1cc(O)c(O)c(O)c1]

Yet another FAS inhibitor is ML356 (selective inhibitors of FAS-TE (thioesterase, last enzymatic step)—Ardecky et al. (2014), Probe reports from the NIH Molecular Libraries Program)—IC50: 334 nM. The structure of ML356 is shown below:

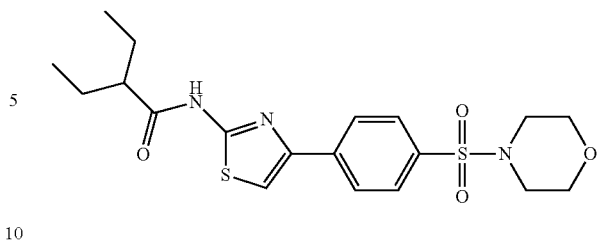

Yet another FAS inhibitor is ZERENEX ZX-IP021842, which structure is shown below:

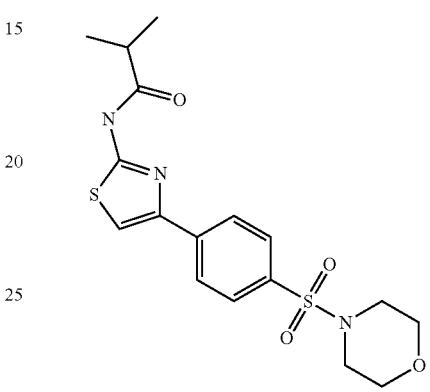

Yet another class of FAS inhibitors are the imidazolin-5-one derivatives, which are described in WO2014/039769 (Janssen Pharma).

Yet another class of FAS inhibitors are compounds claimed in WO2005/117590 (The John Hopkins University).

Yet other classes of FAS inhibitors are compounds disclosed and claimed in WO2015/134790 (Sanford Burnham Med. Res. Inst.), WO2015/095011 (Janssen Pharmaceutica), WO2015/084606 (Janssen Pharmaceutica), WO2014/164749 (Forma Therapeutics), WO2014/164767 (Forma Therapeutics), WO2013/155528 (Fasgen Inc.), WO2013/022927 (Brigham & Womens Hospital), WO2012/064632 (Univ. Wake Forest Health Sciences), WO2011/048018 (Boehringer Ingelheim), WO2011/005790 (Univ. Ohio State Res. Found.), WO2009/149066 (Fasgen Inc.), WO2008/057585 (Fasgen LLC), WO2007/014249 (Univ. Johns Hopkins), WO2007/014247 (Univ. Johns Hopkins), WO2005/117590 (Fasgen LLC), WO2004/034991 (Isis Pharmaceuticals), WO2004/005277 (Fasgen Inc.) and WO2003/088975 (Burnham Inst.).

Medicinal Uses of the FAS Inhibitors:

This disclosure also relates to pharmaceutical compositions containing one or more compounds inhibiting the FAS activity of this disclosure. These compositions can be utilized to achieve the desired pharmacological effect by administration to a patient in need thereof. A patient, for the purpose of this disclosure, is a mammal, including a human, in need of treatment for the particular condition or disease. Therefore, this disclosure includes pharmaceutical compositions that are comprised of a pharmaceutically acceptable carrier and a pharmaceutically effective amount of a compound, or salt thereof, of this disclosure. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount that produces a result or exerts an influence on the particular condition being treated. The compounds of this disclosure can be administered with pharmaceutically acceptable carriers well known in the art using any effective conventional dosage unit forms, including immediate, slow and timed-release preparations, orally, parenterally, topically, nasally, ophthalmically, optically, sublingually, rectally, vaginally, intrathecally, intracerebroventricularly, and the like. In a preferred embodiment, the administration is intrathecally. In another preferred embodiment, the administration is intracerebroventricularly.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatin type containing, for example, surfactants, lubricants, and inert fillers such as lactose, sucrose, calcium phosphate, and corn starch.

In another embodiment, the compounds of this disclosure may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example, talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance, tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above, may also be present.

The pharmaceutical compositions of this disclosure may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of the partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin. Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The parenteral compositions of this disclosure will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents, which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived from a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the disclosure may also be administered in the form of suppositories for rectal administration of the drug. These compositions can be prepared by mixing the drug with a suitable non-irritation excipient, which is solid at ordinary temperatures but liquid at the rectal temperature and will, therefore, melt in the rectum to release the drug. Such materials are, for example, cocoa butter and polyethylene glycol.

Another formulation employed in the methods of this disclosure employs transdermal delivery devices ("patches"). Such transdermal patches may be used to provide continuous or discontinuous infusion of the compounds of the disclosure in controlled amounts. The construction and use of transdermal patches for the delivery of pharmaceutical agents is well known in the art (see, for example, U.S. Pat. No. 5,023,252). Such patches may be constructed for continuous, pulsatile, or on demand delivery of pharmaceutical agents. Controlled release formulations for parenteral administration include liposomal, polymeric microsphere and polymeric gel formulations that are known in the art. It may be desirable or necessary to introduce the pharmaceutical composition to the patient via a mechanical delivery device. The construction and use of mechanical delivery devices for the delivery of pharmaceutical agents is well known in the art. Direct techniques, for example, for administering a drug directly to the brain usually involve placement of a drug delivery catheter into the patient's ventricular system to bypass the blood-brain barrier. One such implantable delivery system used for the transport of agents to specific anatomical regions of the body is described in U.S. Pat. No. 5,011,472.

The compositions of the disclosure can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: M. F. Powell et al., "Compendium of Excipients for Parenteral Formulations," *PDA Journal of Pharmaceutical Science & Technology* 1998, 52(5), 238-311; R. G. Strickley, "Parenteral Formulations of Small Molecule Therapeutics Marketed in the United States (1999)—Part-1," *PDA Journal of Pharmaceutical Science & Technology* 1999, 53(6), 324-349; and S. Nema et al., "Excipients and Their Use in Injectable Products," *PDA Journal of Pharmaceutical Science & Technology* 1997, 51 (4), 166-171.

Pharmaceutical compositions according to this disclosure can be illustrated as follows:

Sterile IV Solution: A 0.01 mg-5 mg/mL solution of the desired compound of this disclosure can be made using sterile, injectable water, and the pH is adjusted if necessary. The solution is diluted for administration to 0.01-2 mg/mL with sterile 5% dextrose and is administered as an IV infusion over about 60 minutes.

Lyophilized powder for IV administration: A sterile preparation can be prepared with (i) 1-1000 mg of the desired compound of this disclosure as a lyophilized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.01-1 mg/mL, and is administered either IV bolus or by IV infusion over 15-60 minutes.

Intramuscular suspension: The following solution or suspension can be prepared, for intramuscular injection:

0.01 mg-50 mg/mL of the desired, water-insoluble compound of this disclosure
5 mg/mL sodium carboxymethylcellulose
4 mg/mL TWEEN® 80
9 mg/mL sodium chloride
9 mg/mL benzyl alcohol Combination Therapies The compounds of this disclosure can be administered as the sole pharmaceutical agent or in combination with one or more other pharmaceutical agents where the combination causes no unacceptable adverse effects. This disclosure relates also to such combinations. For example, the compounds of this disclosure can be combined with known medicines for the treatment of early-onset Parkinson's disease, particularly Parkinson's disease patients carrying loss of function mutations in PINK1 or PARKIN genes.

The term "treating" or "treatment" as stated throughout this document is used conventionally, e.g., the management or care of a subject for the purpose of combating, alleviating, reducing, relieving, improving the condition of, etc., of a disease or disorder, such as early-onset Parkinson's disease.

In a particular preferred embodiment the "molecules" may be administered by a method close to the place of onset. Preferably a continuous infusion is used and includes the continuous subcutaneous delivery via an osmotic minipump.

In another embodiment, "close to the onset" administration is an intrathecal administration.

In another embodiment, "close to the onset" administration is an intracerebroventricular administration. Thus, in a particular embodiment, the infusion with a composition comprising a molecule of the disclosure is intrathecal. Intrathecal administration can, for example, be performed by means of surgically implanting a pump and running a catheter to the spine or in the skull.

Dose and Administration

Based upon standard laboratory techniques known to evaluate compounds useful for the treatment of early-onset Parkinson's disease, by standard toxicity tests and by standard pharmacological assays for the determination of treatment of the conditions identified above in mammals, and by comparison of these results with the results of known medicaments that are used to treat these conditions, the effective dosage of the compounds of this disclosure can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 150 mg of active ingredient, and can be administered one or more times per day or less than once a day. The average daily dosage for administration by injection, including intravenous, intramuscular, subcutaneous, intrathecal, intraceroventricularly and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

It is evident for the skilled artisan that the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like: The desired mode of treatment and number of doses of a compound of this disclosure or a pharmaceutically acceptable salt or ester or composition thereof can be ascertained by those skilled in the art using conventional treatment tests.

Examples

1. Suppressor Screen in *Drosophila* Homozygous PINK1 Mutants

Figure 2:
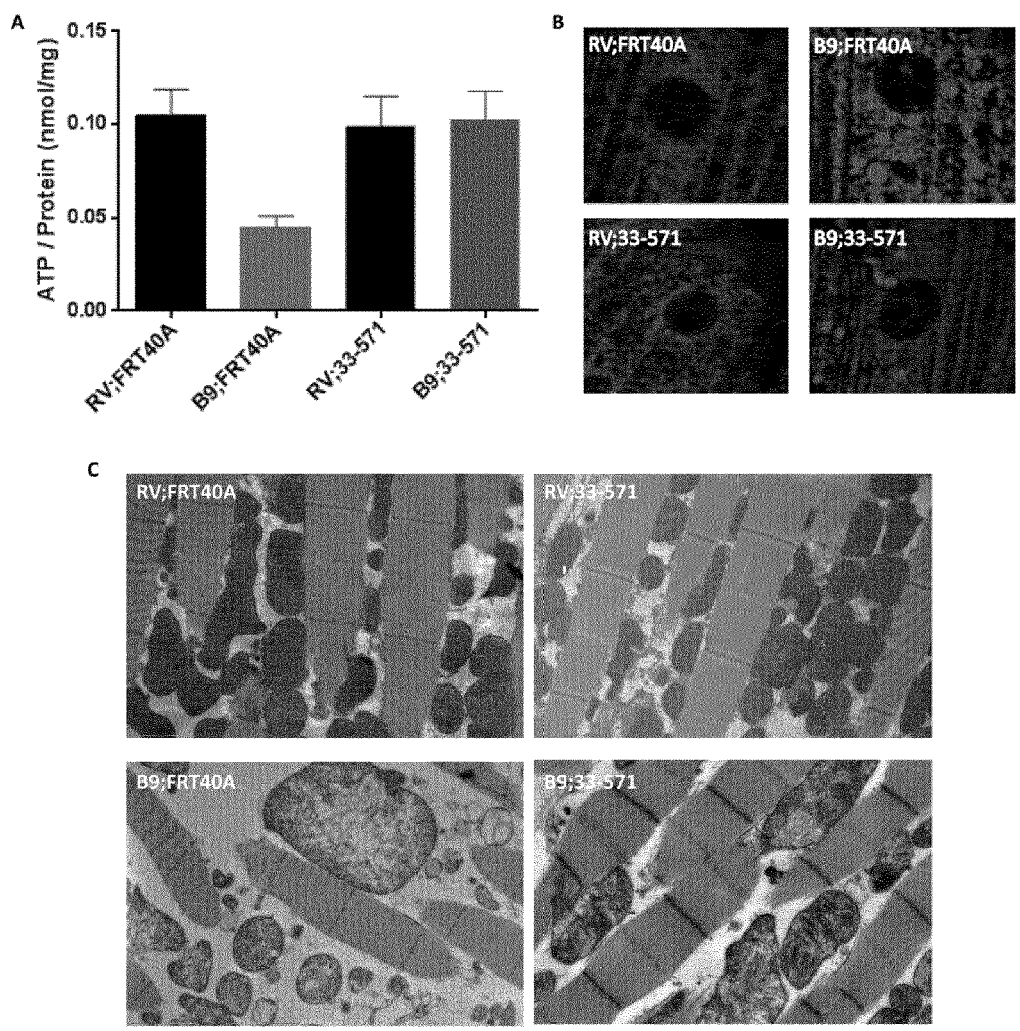
FIG. 2: Heterozygous loss of v(2)k05816 can rescue mitochondrial defects in PINK1 mutant flies. (Panel A) ATP levels of control (RV; FRT40A, black bars) and PINK1 mutant (B9; FRT40A, gray bars) flies. Heterozygous loss of v(2)k05816 (33-571) elevates ATP levels compared to control allele. (Panel B) Mitochondrial morphology, labeled with ATP synthase subunit antibody, in loss of PINK1 shows swollen mitochondria that is reduced upon dominant v(2) k05816 mutation (B9; 33-571). (Panel C) Electron microscopy images of mitochondria in adult thorax muscle. In PINK1 mutant flies (B9; FRT40A), cristae structure of the mitochondria is defective/absent and mitochondria are enlarged. In B9; 33-571 flies, mitochondria still appear to be swollen, but cristae structure is rescued.

In *Drosophila melanogaster*, loss of PINK1 function results in very clear phenotypes, including reduced flight ability and mitochondrial defects such as reduced Complex I activity of the electron transport chain that results in reduced ATP levels and disruption of the mitochondrial membrane potential, and defective mitochondrial morphology. Although PINK phenotypes are well characterized, only few mechanisms that can be employed to suppress them have been identified. To elucidate novel pathways that can be exploited to suppress PINK1-dependent defects, a dominant modifier screen was performed. Mutations in one of the genes that significantly suppresses the PINK1 mutant flight phenotype map to v(2)k05816 encoding the *Drosophila* homologue of the mammalian Fatty Acid Synthase (FASN). Different alleles of this gene were shown to induce in a heterozygous condition a rescue of the PINK1 mutant flight phenotype (see FIG. 1), demonstrating that partial (heterozygous) loss of FASN is already sufficient to rescue defects associated with loss of PINK. Furthermore, heterozygous mutations in v(2)k05816 rescue the lower ATP levels seen in PINK1 mutants as well as the defective mitochondrial morphology at the level of both mitochondrial network and cristae structure (see FIG. 2, Panels A-C). Hence, partial deletion of FASN function rescues mitochondrial and systemic defects associated with the loss of PINK1 in fruit flies.

2. Pharmacological Inhibitors of FAS can Rescue PINK1 Mutant Flies

Figure 3:
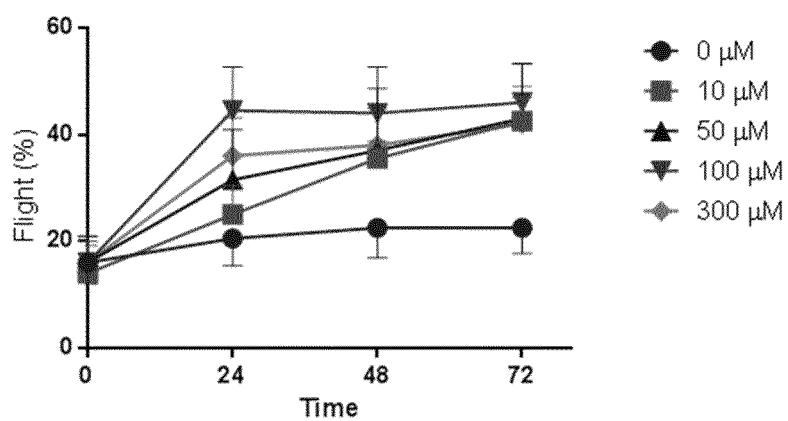
FIG. 3: Dose response curve of flight ability of PINK1 mutant flies fed with cerulenin. PINK1 mutant flies were placed on food supplemented with different concentrations of cerulenin. Flight assay was performed every 24 hours and flies showed increased flight ability with cerulenin feeding.

FASN is a 273 kDa protein that produces palmitate, which is a precursor of fatty acids in a seven-step enzymatic reaction. FASN uses malonyl CoA and acetyl CoA as substrates. Several inhibitors of FASN function exist. Tests were performed to determine whether defective flight in PINK1 mutants could be pharmacologically rescued. One-day-old PINK1 and control flies were placed on food mixed with different concentrations of the FASN inhibitor cerulenin that inhibits the first step of the biosynthetic process catalyzed by FASN and tested if the flies were able to fly. Indeed, a dose-response effect was observed on the ability of PINK1 mutants to fly when higher doses of cerulenin were fed to the flies (see FIG. 3). It was noted that this is an acute effect that occurs in a few days and that the flight (and mitochondrial) defects that were observable in one-day-old PINK1 mutants are acutely rescued.

Figure 7:
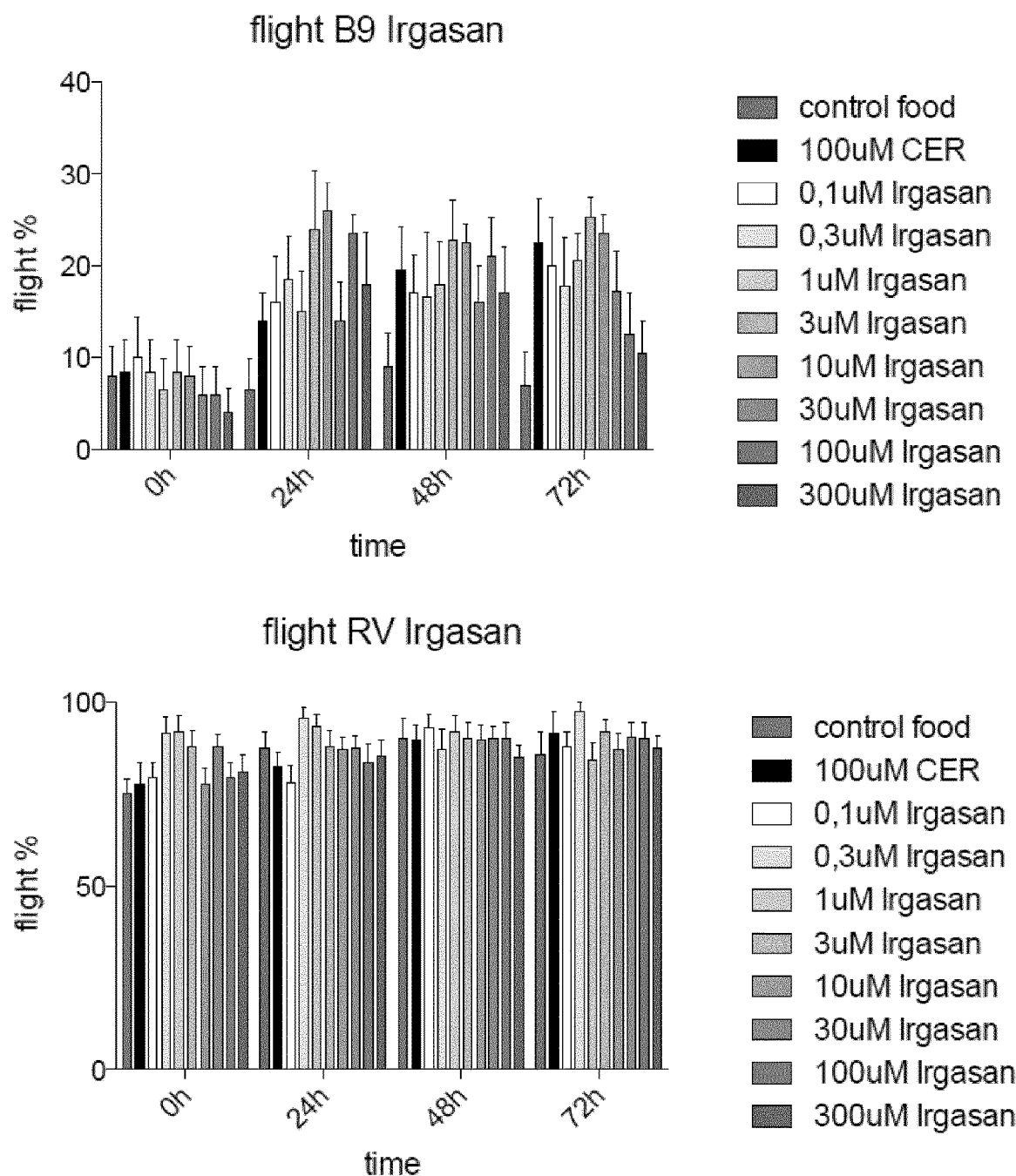
FIG. 7: Dose response curve of flight ability of PINK1 mutant flies (B9) fed with irgasan. The upper part of the figure depicts the PINK1 mutant flies fed with control food (left bar for each of the time windows 0 h, 24 h, 48 h and 72 h), the second bar is 100 µM cerulin (CER), the other bars are different concentrations of irgasan. The lower part of the figure depicts the wild-type flies (RV) fed with control food, cerulin (CER) and different concentrations of irgasan.

The effect on restoring the flight ability of PINK1 mutant flies with a second FAS inhibitor (irgasan) is depicted in FIG. 7). A dose response study with irgasan shows that concentrations between 1-10 µM irgasan clearly enhance the flight ability. The lower part of FIG. 7 shows the effect of irgasan on wild-type flies.

Figure 4:
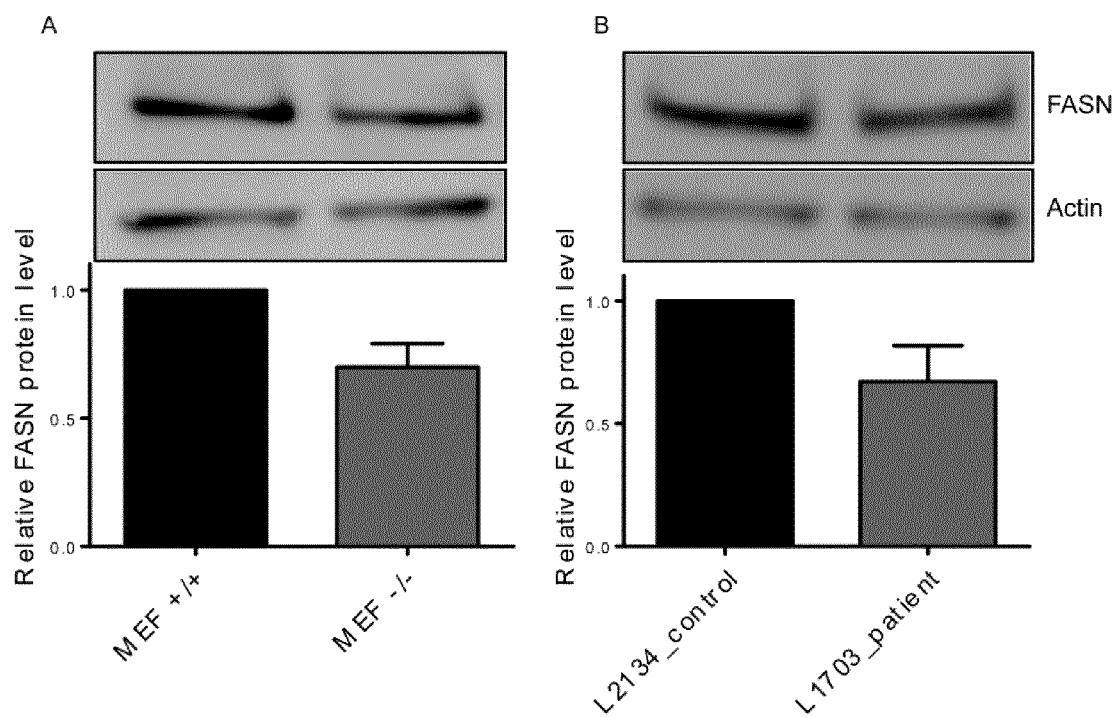
FIG. 4: Protein levels of FASN. FASN protein levels are reduced in PINK$^{-/-}$ MEFs (Panel A) and fibroblasts isolated from patients carrying mutations in PINK1 (L1703) (Panel B) compared to controls (PINK1$^{+/+}$ MEF and L2134 controls).

3. Pharmacological Inhibitors of FAS can Rescue PINK1 Homozygous Mutant Mammalian Cells To elucidate if the mechanism by which reduction of FASN results in rescue of loss of PINK1 is evolutionary or conserved and to start exploring the mechanism of suppression, mammalian cell culture was employed. First, testing was performed to determine if the FASN protein levels were changed as a consequence of loss of PINK1 function. Indeed, in PINK1 mice embryonic fibroblasts (MEFs) and in fibroblasts isolated from patients carrying PINK mutations, FASN levels are lower (FIG. 4, Panels A and B). These data suggest that in cells mutant for PINK1, a compensatory mechanism is already active to lower FASN levels. The data from flies indicate that further lowering FASN levels is beneficial for mitochondrial function.

Figure 5:
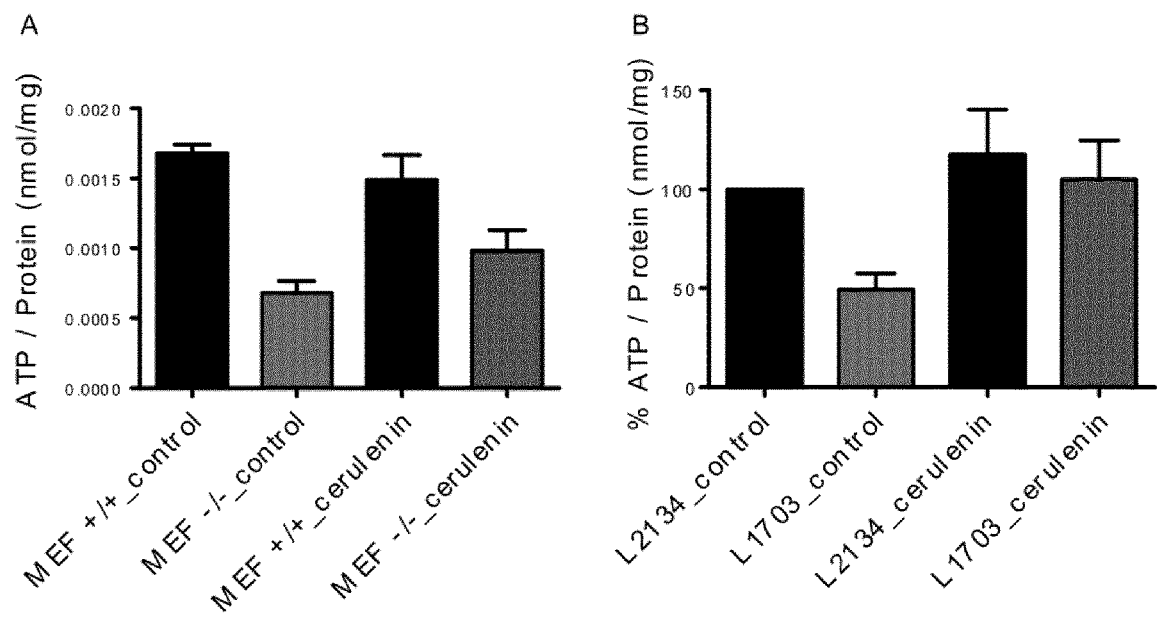
FIG. 5: ATP levels of cells treated with the FASN inhibitor cerulenin. PINK1$^{-/-}$ MEFs (Panel A) and fibroblasts from patients carrying mutations in PINK1 (L1703) (Panel B) were treated with cerulenin and showed elevated ATP levels compared to untreated cells. Cerulenin did not have an effect on control cells.

To directly test if further lowering FASN activity in PINK mutant cells rescues the mitochondrial dysfunction in these cells, ATP levels were tested. While PINK1 mutant cells show lower ATP levels as a result of mitochondrial dysfunction, supplementing cerulenin to the cells resulted in increased levels of ATP in both the MEFs and the patient-derived fibroblasts (see FIG. 5, Panels A and B). Thus, the inhibition of FASN with an inhibitor rescues in flies and cells isolated from mice and patients the PINK1-induced mitochondrial defects.

4. Pharmacological Inhibitors of FAS Also Rescue PARKIN Mutant Flies

Figure 6:
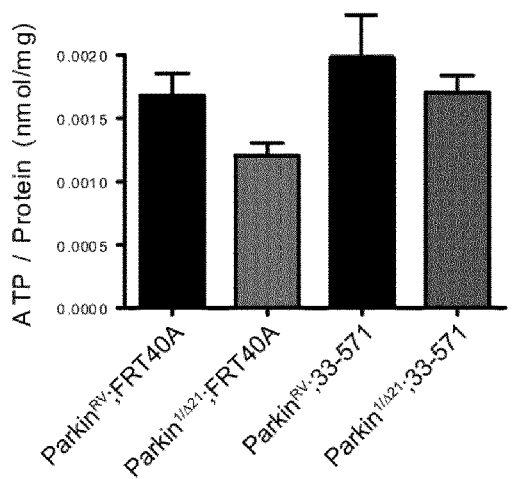
FIG. 6: ATP levels of PARKIN mutant flies. The reduced levels of ATP in parkin mutant flies can be rescued by removing one copy of FASN (parkin$^{1/\Delta 21}$; 33-571).

Aside from its function in Complex I, PINK1 has also been identified as a factor in the clearance of defective mitochondria (=mitophagy) together with PARKIN, another protein involved in PD. Therefore, tests were performed to determine whether heterozygous loss of FASN could induce a rescue in PARKIN mutant flies. PARKIN mutant flies show reduced levels of ATP and this could be rescued with a dominant mutation for FASN (see FIG. 6). As a result, it was shown that the loss of FASN suppresses the phenotypes linked to the PD-related proteins PINK1 and PARKIN and that the use of FAS inhibitors can be used to manufacture a medicament for the treatment of mutation carriers of PD carrying mutations in PINK or PARKIN genes.

5. Reduced Cardiolipin Levels in PINK1 Mutants are Rescued by Inhibition of FASN Genetic or pharmacological inhibition of FASN in flies and in MEFs shows lower palmitate levels compared to mock (control medium) treatment. Surprisingly, PINK1 null mutant flies and PINK1$^{-/-}$ mutant MEFs already show lower palmitate levels even when FASN is not inhibited. These results may be at least partially explained by the observation that PINK-mutant cells harbor lower FASN protein levels as revealed by Western blotting. Nonetheless, when FASN activity was lowered further in PINK1$^{-/-}$ mutants, either by genetic or by pharmacological inhibition, the palmitate levels drop further. Hence, inhibition of FASN function results in lower palmitate levels in controls and PINK1 mutants. Palmitate is involved in several downstream pathways and increased palmitate levels by adding excess exogenous palmitate were shown to inhibit the production of cardiolipin (CL), a lipid that is exclusive to the inner mitochondrial membrane and to the membrane of bacteria. Only unsaturated phosphatidylglycerol (PG) is a good substrate for CL synthase (Bobyleva et al. (1997) *Biochem. Mol. Biol. Int.* 41:469-480) and high levels of palmitate shift the balance toward more saturated PG (Ostrander et al. (2001)

*J. Biol. Chem.* 276:38061-38067). Opposite to this, it was confirmed that inhibition of FASN results in more unsaturated PG, while wondering if FASN inhibition results in increased CL levels. Shotgun lipidomics of mitochondrial fractions revealed lower CL levels in PINK$^{-/-}$ MEFs compared to control MEFs. Interestingly, inhibition of FASN using Cerulenin in PINK$^{-/-}$ MEFs almost completely restored the levels of all the CL species that were assessed back to control levels. Hence, it was concluded that loss of FASN function results in more mitochondrial CL in PINK1-/- mutants.

6. Cardiolipin Increases Complex I Function

PINK1-/- mutants harbor lower enzymatic activity of Complex I (Morais et al. (2009) *EMBO Mol. Med.* 1:99-111). Therefore, it was questioned as to whether the rescuing-effect of inhibition of FASN acts by bypassing this Complex I defect. It was found that partial inhibition of FASN using genetics or pharmacology restores the defective Complex I enzymatic activity in PINK1 mutant flies and MEFs back to control levels. The inefficient electron transport between Complex I and ubiquinone in PINK1 mutants was shown to be the result of an inability to maintain phosphorylation of Serine 250 in the Complex I subunit NdufA10 (Morais et al. (2014) *Science* 344:203-207). Indeed, mitochondria from engineered mammalian cells expressing only phosphorylation-deficient NdufA10S250A transfer electrons less efficiently from Complex I to ubiquinone similar to PINK1 mutant mitochondria. Interestingly, it was found that pharmacological inhibition of FASN resulted in a complete restoration of this activity, indicating that inhibition of FASN bypasses these ETC defects. CL stabilizes cristae and ETC supercomplexes (Friedman et al. (2015) *Elife* 4), but a role for this lipid in the direct regulation of electron transport between Complex I and ubiquinone in animal mitochondria has not been assessed. Therefore, the ability of CL to bypass the electron transfer defect in Complex I was directly tested. Mitochondria from PINK1 null mutant flies or PINK1 MEFs were isolated and incubated with CL after sonicating, allowing the lipid to incorporate. This manipulation showed a strong rescue of the electron transfer activity defects in PINK1 mutant Complex I. The measurements are independent of a possible effect of CL on ETC supercomplexes because the freeze-thaw steps and sonication that were used to prepare the samples were shown to disrupt such ETC supercomplexes. Furthermore, Complex I defects in NdufA10S205A phosphorylation-deficient cells are also efficiently rescued when the mitochondria were incubated with CL. Hence, it was concluded that CL facilitates electron transport between Complex I and ubiquinone and increasing CL levels is sufficient to bypass the defects in PINK1 and NdufA10S205A mutants.

Materials and Methods

1. Feeding Experiments

One-day-old adult flies were placed on molasses medium supplemented with 100 µM Cerulenin (Enzo Life Sciences) or 3 µM Irgasan (Sigma) (2.5% final ethanol concentration) or supplemented with 2.5% ethanol for control medium. The animals were kept on these media for 72 hours and tested for flight or ATP levels. To determine mitochondrial morphology, embryos were placed on molasses medium supplemented with 100 µM Cerulenin (2.5% final ethanol concentration) or supplemented with 2.5% ethanol for control medium and grown to the third instar larval stage. These third instar larvae were dissected and used for experiments (see below).

Cells were treated with 10 µM Cerulenin (0.1% ethanol) or control medium supplemented with 0.1% ethanol.

2. Flight and Survival

The flight assay was conducted on male flies using batches of five flies each. The flies were placed in an empty vial and gently tapped. The flies that were able to fly were given a score of 1, while those that did not fly, were given a score of 0.

For survival, the latest survival stage of animals is indicated for animals that were reared on grape juice plates (above) with yeast paste and that were in uncrowded conditions.

3. ATP Determination

ATP levels were determined as previously described (Morais et al. (2014) *Science* 344:203-207) using an ATP determination kit (Invitrogen) according to supplier's protocol. Luminescence was measured on a luminometer (Biorad) and values were normalized to total protein content (Bradford method).

4. Mitochondrial Isolation and Complex I Activity Measurements

Mitochondria were isolated by standard differential centrifugation. Mitochondrial isolates were sonicated and used to measure Complex I activity. In short, to measure NADH: $O_2$ oxidoreductase activity, mitochondrial isolates were buffered in medium containing phosphate buffer (0.1 M pH 7.4), BSA (10 mg/ml), NADH (1 mM) and KCN (30 mM). Decylubiquinone, a ubiquinone analog, was added to accept the electrons from Complex I and to activate the reaction. The activity of NADH oxidation was spectrophotometrically followed at 340 nm at 37° C. and corrected for rotenone-insensitive NADH oxidation. Values were normalized to citrate synthase activity.

For CL incubation, isolated mitochondria underwent freeze-thaw steps and sonication to disrupt mitochondrial membranes and they were then incubated with various concentrations of a CL mixture containing 14:1(3)-15:1, 15:0(3)-16:1, 22:1(3)-14:1 and 24:1(3)-14:1 species of CL (avantilipids) at 37° C. prior to Complex I activity measurements.

5. Determination of Mitochondrial Morphology

Larvae were dissected in HL-3 and larval fillets were fixed in 4% formaldehyde in PBS for 20 minutes and permeabilized with 0.4% TRITON® X-100. Primary antibody anti-ATP synthase B mAb (1:200; Abcam) was used to visualize mitochondria. Secondary antibody was goat anti-mouse ALEXA® 555 (1:1000). Images were visualized with an LSM510META confocal microscope and a 63× NA 1.4 oil lens. Images were quantified using the "analyzing particles" plugin in ImageJ where rounded mitochondria were automatically detected and counted.

6. Free Fatty Acid Measurement

Samples were homogenized in 5% isopropanol and 5% TRITON® X-100 and prepared according to the manufacturer's protocol (BioAssay Systems). The amount of free palmitate was analyzed by measuring optic density at 570 nm on a multilabel reader. Values were normalized to protein content.

7. Lipid Analysis

Mitochondria were isolated and resuspended in ammonium bicarbonate buffer. Lipids were extracted and analyzed using shotgun mass spectrometry (lipotype). In short, using Chloroform and Methanol, lipids were extracted via a two-step lipid extraction process. These extracted lipids were then immediately subjected to mass spectrometric analysis. Lipid data were acquired on a hybrid quadrupole/ORBITRAP® mass spectrometer (Q-Exactive, Thermo-Fisher)

equipped with an automated nanoflow electrospray ion source (TRIVERSA NANOMATE® Advion) in both positive and negative ion mode. LIPOTYPE® XPLORER® was used to identify lipids on unprocessed mass spectra.

8. Statistics

Statistical analyses were performed using the GRAPHPAD PRISM™ program and significance was evaluated using 2-tailed Student's t test. P values were considered significant when they were lower than 0.05.

The invention claimed is:

1. A method of treating a subject with early-onset Parkinson's disease, the method comprising:
   administering to the subject a fatty acid synthase (FAS) inhibitor (FAS inhibitor) so as to treat the subject's early-onset Parkinson's disease,
   wherein the FAS inhibitor is selected from the group consisting of an siRNA directed against FASN, an artificial microRNA directed against FASN, an antisense molecule directed against FASN, a ribozyme directed against FASN, and a small molecule directed against FAS,
   wherein the subject's genome has a loss of function PINK1 gene mutation and/or has a PARKIN gene mutation; and
   wherein the FAS inhibitor is administered as the sole pharmaceutical agent.

2. The method according to claim 1, wherein the subject has a loss of function gene mutation in PINK1 in a heterozygous state.

3. The method according to claim 1, wherein the subject has a loss of function gene mutation in PINK1 in a homozygous state.

4. The method according to claim 1, wherein the subject has a loss of function gene mutation in PARKIN in a heterozygous state.

5. The method according to claim 1, wherein the subject has a loss of function gene mutation in PARKIN in a homozygous state.

6. A method of treating a subject with early-onset Parkinson's disease, the method comprising:
   identifying that the subject's genome has a loss of function PINK1 gene mutation and/or has a PARKIN gene mutation
   administering to the subject a fatty acid synthase (FAS) inhibitor (FAS inhibitor) so as to treat the subject's early-onset Parkinson's disease,
   wherein the FAS inhibitor is selected from the group consisting of an siRNA directed against FASN, an artificial microRNA directed against FASN, an antisense molecule directed against FASN, a ribozyme directed against FASN, and a small molecule directed against FAS; and
   wherein the FAS inhibitor is administered as the sole pharmaceutical agent.

* * * * *